US00PP27676P2

(12) United States Plant Patent
van de Meer

(10) Patent No.: US PP27,676 P2
(45) Date of Patent: Feb. 14, 2017

(54) ***ASTILBE* PLANT NAMED 'CHOCOLATE CHERRY'**

(50) Latin Name: ***Astilbe japonica*×*Astilbe arendsii***
Varietal Denomination: Chocolate Cherry

(71) Applicant: Hans van de Meer, Nieuwe Wetering (NL)

(72) Inventor: Hans van de Meer, Nieuwe Wetering (NL)

(73) Assignee: Compass Plants B.V., Hillegom (NL)

( * ) Notice: Subject to any disclaimer, the term of this patent is extended or adjusted under 35 U.S.C. 154(b) by 0 days.

(21) Appl. No.: 14/998,425

(22) Filed: Dec. 31, 2015

(51) Int. Cl.
*A01H 5/02* (2006.01)

(52) U.S. Cl.
USPC ..... Plt./407

(58) Field of Classification Search
USPC ..... Plt./407
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Astilbe* plant named 'Chocolate Cherry', characterized by its broadly upright plant habit; dark green and brown-colored leaves; freely and uniformly flowering habit; red purple-colored flowers positioned just above the foliar plane on strong and brownish red-colored stems; and good container and garden performance.

3 Drawing Sheets

Botanical designation: *Astilbe japonica*×*Astilbe arendsii*.
Cultivar denomination: 'CHOCOLATE CHERRY'.

BACKGROUND OF THE INVENTION

The present invention relates to a new and distinct cultivar of *Astilbe*, botanically known as *Astilbe japonica*×*Astilbe arendsii* and hereinafter referred to by the name 'Chocolate Cherry'.

The new *Astilbe* plant is a product of a planned breeding program conducted by the Inventor in Nieuwe Wetering, The Netherlands. The objective of the breeding program was to create new uniform and freely flowering *Astilbe* plants with attractive leaf and flower coloration.

The new *Astilbe* plant originated from a cross-pollination made by the Inventor in 2010 in Nieuwe Wetering, The Netherlands, of an unnamed selection of *Astilbe japonica*, not patented, as the female, or seed, parent with an unnamed selection of *Astilbe arendsii*, not patented, as the male, or pollen, parent. The new *Astilbe* plant was discovered and selected by the Inventor as a single flowering plant from within the progeny of the stated cross-pollination in a controlled greenhouse environment in Nieuwe Wetering, The Netherlands in 2012.

Asexual reproduction of the new *Astilbe* plant by vegetative divisions in a controlled environment in Nieuwe Wetering, The Netherlands since December, 2012 has shown that the unique features of this new *Astilbe* plant are stable and reproduced true to type in successive generations.

SUMMARY OF THE INVENTION

Plants of the new *Astilbe* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Chocolate Cherry'. These characteristics in combination distinguish 'Chocolate Cherry' as a new and distinct *Astilbe* plant:

1. Broadly upright plant habit.
2. Dark green and brown-colored leaves.
3. Freely and uniformly flowering habit.
4. Red purple-colored flowers positioned just above the foliar plane on strong and brownish red-colored stems.
5. Good container and garden performance.

Plants of the new *Astilbe* differ primarily from plants of the parent selections in the following characteristics:

1. Plants of the new *Astilbe* are taller than plants of the parent selections.
2. Plants of the new *Astilbe* have brown and green-colored leaves whereas plants of the parent selections have green-colored leaves.
3. Plants of the new *Astilbe* are more freely flowering than plants of the parent selections.
4. Plants of the new *Astilbe* have broader inflorescences than plants of the parent selections.

Plants of the new *Astilbe* can be compared to plants of *Astilbe arendsii* 'Fanal', not patented. In side-by-side comparisons conducted in Hillegom, The Netherlands, plants of the new *Astilbe* and 'Fanal' differed in the following characteristics:

1. Plants of the new *Astilbe* were taller than plants of 'Fanal'.
2. Plants of the new *Astilbe* had brown and green-colored leaves whereas plants of 'Fanal' had green-colored leaves.
3. Plants of the new *Astilbe* were more freely flowering than plants of 'Fanal'.
4. Plants of the new *Astilbe* had larger inflorescences than plants of 'Fanal'.
5. Inflorescences of plants of the new *Astilbe* and 'Fanal' differed in peduncle and pedicel color as plants of 'Fanal' had green-colored peduncles and pedicels.

BRIEF DESCRIPTION OF THE PHOTOGRAPHS

The accompanying colored photographs illustrate the overall appearance of the new *Astilbe* plant showing the colors as true as it is reasonably possible to obtain in colored reproductions of this type. Colors in the photographs may differ slightly from the color values cited in the detailed botanical description which accurately describe the colors of the new *Astilbe* plant.

The photograph on the first sheet comprises a side perspective view of a typical flowering plant of 'Chocolate Cherry' grown in a container.

The photograph on the second sheet is a close-up view of typical leaves of 'Chocolate Cherry'.

The photograph on the third sheet is a close-up view of typical inflorescences of 'Chocolate Cherry'.

DETAILED BOTANICAL DESCRIPTION

The aforementioned photographs and following observations, measurements and values describe plants grown in 21-cm containers during the late summer and early autumn in an outdoor nursery in Hillegom, The Netherlands and under cultural practices typical of commercial *Astilbe* production. During the production of the plants, day temperatures ranged from 14° C. to 32° C. and night temperatures ranged from 6° C. to 18° C. Plants were one year old when the photographs and description were taken. In the following description, color references are made to The Royal Horticultural Society Colour Chart, 2015 Edition, except where general terms of ordinary dictionary significance are used.

Botanical classification: *Astilbe japonica*×*Astilbe arendsii* 'Chocolate Cherry'.

Parentage:

*Female, or seed, parent*.—Unnamed *Astilbe japonica* seedling selection, not patented.

*Male, or pollen, parent*.—Unnamed *Astilbe arendsii* seedling selection, not patented.

Propagation:

*Type*.—By divisions.

*Time to initiate roots*.—About three weeks at temperatures about 20° C.

*Root description*.—Thick, fleshy.

*Rooting habit*.—Freely branching; dense.

Plant description:

*Plant form and growth habit*.—Herbaceous perennial; broadly upright plant habit with inflorescences held just above the foliar plane; plant shape roughly triangular; flowering stems and leaves basal; freely flowering with numerous basal branches developing per plant; moderately vigorous growth habit; freely and uniformly flowering habit.

*Growth rate*.—Moderate to fast; from divisions, about ten months are required to produce fully-grown flowering plants in containers.

*Plant height* (*soil level to top of foliar plane*).—About 38.5 cm.

*Plant height* (*soil level to top of inflorescences*).—About 75.8 cm.

*Plant width* (*spread*).—About 57.4 cm.

*Stem description*.—Length: About 32.4 cm. Diameter: About 4 mm. Internode length: About 12.6 cm. Strength: Strong, sturdy. Texture: Moderately pubescent. Luster: Slightly glossy. Color: Close to 144A, 174A and 182B.

Leaf description:

*Arrangement*.—Alternate in basal rosettes; biternately compound; about 16 to 39 leaflets per leaf.

*Leaf length* (*excluding petiole*).—About 23.7 cm.

*Leaf width*.—About 25.2 cm.

*Leaflet length*.—About 6.8 cm.

*Leaflet width*.—About 4.2 cm.

*Leaf shape*.—Roughly deltoid to broadly ovate in outline.

*Leaflet shape*.—Broadly elliptic to ovate.

*Leaflet apex*.—Apiculate.

*Leaflet base*.—Attenuate.

*Leaflet margin*.—Biserrate.

*Leaflet texture, upper and lower surfaces*.—Sparsely to moderately pubescent; rough.

*Leaflet luster, upper and lower surfaces*.—Slightly glossy.

*Leaflet venation pattern*.—Pinnate.

*Leaflet color*.—Developing leaflets, upper surface: Close to 200B. Developing leaflets, lower surface: Slightly lighter than between N186C and 200B. Fully expanded leaflets, upper surface: Close to NN137B; venation, close to 144A. Fully expanded leaflets, lower surface: Close to between 146A and 147B; venation, close to 145B.

*Leaf petiole length*.—About 29.3 cm.

*Leaf petiole diameter*.—About 2.5 mm.

*Leaflet petiole length*.—About 3.5 cm.

*Leaflet petiole width*.—About 1.5 mm.

*Leaf and leaflet petiole texture, upper and lower surfaces*.—Smooth, glabrous.

*Leaf and leaflet petiole color, upper and lower surfaces*.—Close to between N199A and N199C.

Flower description:

*Flower type and flowering habit*.—Single rotate flowers arranged on terminal panicles; flowers face upright, outwardly or drooping depending on position on the inflorescence; panicles roughly conical in shape; freely and uniformly flowering habit with about 3,000 flowers developing per inflorescence.

*Fragrance*.—Faint; sweet, pleasant.

*Natural flowering season*.—Plants begin flowering about ten months after planting; continuously flowering from early to late summer in The Netherlands.

*Postproduction longevity*.—Flowers last about ten days on the plant; flowers persistent.

*Flower buds*.—Height: About 2 mm. Diameter: About 1.8 mm. Shape: Broadly ovoid. Color: Close to 60B.

*Inflorescence height*.—About 35.2 cm.

*Inflorescence diameter*.—About 11.5 cm.

*Flower diameter*.—About 1 cm.

*Flower depth*.—About 7 mm.

*Petals*.—Quantity per flower: Typically five in a single whorl. Length: About 7 mm. Lobe width: About 0.5 mm. Shape: Oblanceolate. Apex: Acute. Margin: Entire. Texture, upper and lower surfaces: Smooth, glabrous. Luster, upper and lower surfaces: Dull. Color: Developing petals, upper and lower surfaces: Close to 61B. Fully expanded petals, upper and lower surfaces: Close to N66D; color does not change with development.

*Sepals*.—Quantity per flower: Typically five in a single whorl, fused towards the base; campanulate-shaped calyx. Length: About 2.5 mm. Width: About 0.8 mm. Shape: Ovate. Apex: Acute. Margin: Entire. Texture, upper and lower surfaces: Smooth, glabrous. Luster, upper and lower surfaces: Dull. Color: Developing sepals, upper and lower surfaces: Close to N66B.

Fully expanded sepals, upper and lower surfaces: Close to 67B; towards the apex, close to 67A.

*Peduncles*.—Length: About 43.7 cm. Diameter: About 3 mm. Angle: Erect to about 40° from vertical. Strength: Strong. Texture: Smooth, glabrous. Color: Close to 187C.

*Pedicels*.—Length: About 0.5 mm. Diameter: About 0.5 mm. Angle: About 50° from peduncle axis. Strength: Moderately strong. Texture: Smooth, glabrous. Color: Close to 67B.

*Reproductive organs*.—Stamens: Quantity per flower: Typically ten. Filament length: About 2.5 mm. Filament color: Close to N66D. Anther shape: Ovate, basifixed. Anther length: About 0.5 mm. Anther color: Close to N186B to N186C. Pollen amount: Scarce. Pollen color: Close to 156D. Pistils: Quantity per flower: Typically two. Pistil length: About 3 mm. Stigma shape: Club-shaped. Stigma color: Close to N66D. Style length: About 2.75 mm. Style color: Close to N66D. Ovary color: Close to N66D.

*Seeds and fruits*.—Seed and fruit development have not been observed on plants of the new *Astilbe*.

Disease & pest resistance: Plants of the new *Astilbe* have not been noted to be resistant to pathogens and pests common to *Astilbe* plants.

Garden performance: Plants of the new *Astilbe* have been observed to have good garden performance and tolerate rain, wind and high temperatures of about 35° C. Plants of the new *Astilbe* have been observed to be hardy to USDA Hardiness Zone 5.

It is claimed:

1. A new and distinct *Astilbe* plant named 'Chocolate Cherry' as illustrated and described.

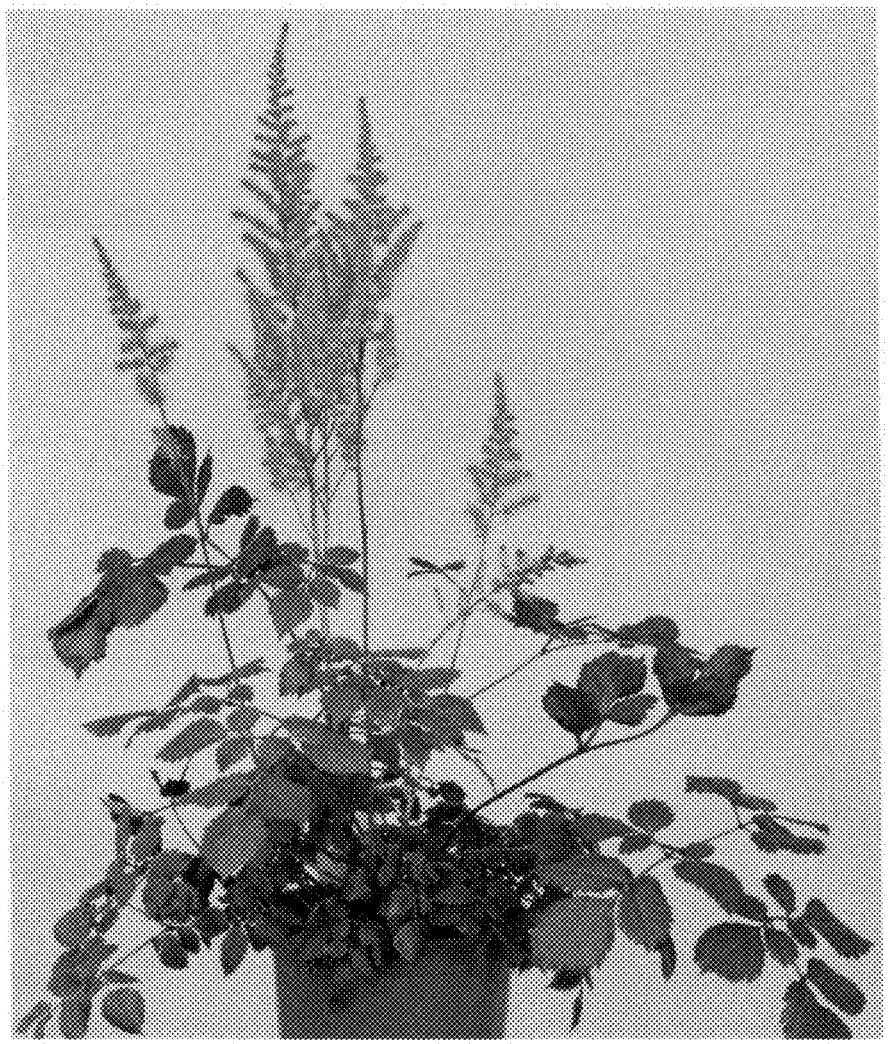

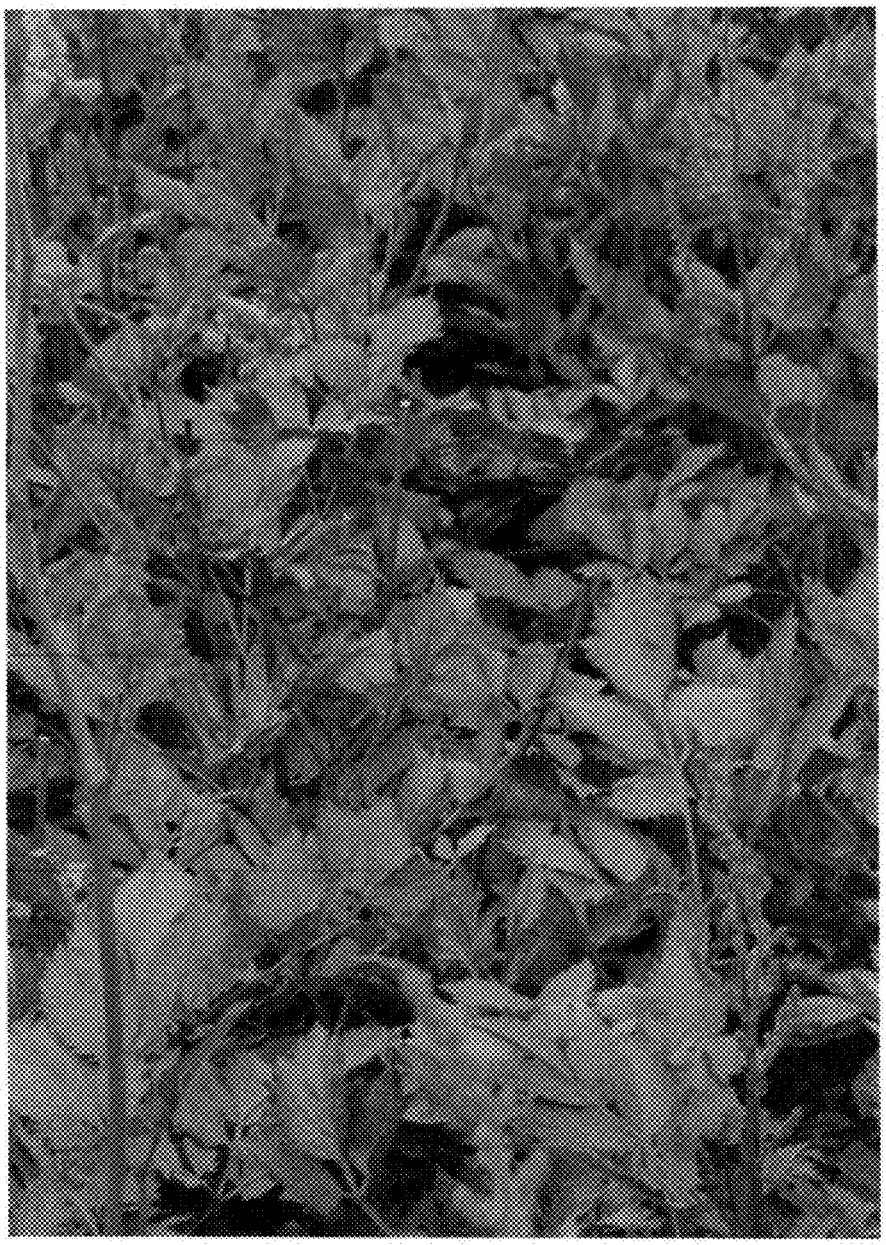

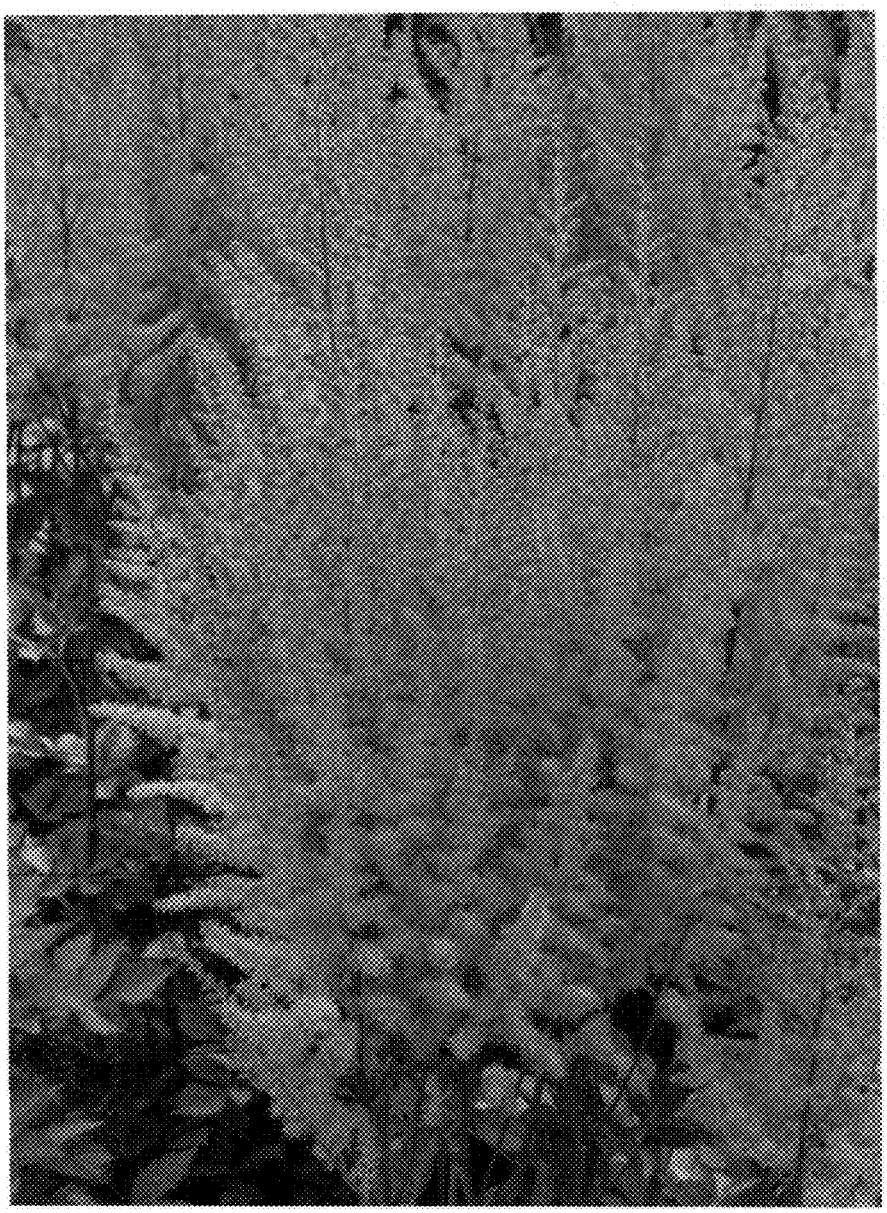

* * * * *